United States Patent [19]

Durette et al.

[11] Patent Number: 4,868,155

[45] Date of Patent: Sep. 19, 1989

[54] DIPEPTIDYL 4-0-,6-0-ACYL-2-AMINO-2-DEOXY-D-GLUCOSE COMPOSITIONS AND METHODS OF USE IN AIDS-IMMUNOCOMPROMISED HUMAN HOSTS

[75] Inventors: Philippe L. Durette, New Providence; Conrad P. Dorn, Plainfield, both of N.J.

[73] Assignee: Merck & Co., Inc., Rahway, N.J.

[21] Appl. No.: 105,055

[22] Filed: Oct. 5, 1987

[51] Int. Cl.$^4$ .................... A61K 37/02; A61K 39/00; C07C 103/52
[52] U.S. Cl. ......................................... 514/19; 514/2; 514/8; 514/9; 514/21; 514/42; 514/44; 514/46; 514/50; 514/75; 514/78; 514/357; 260/396 R
[58] Field of Search ...................... 424/88, 89; 514/19, 514/8, 2, 9, 21, 42, 44, 46, 50, 75, 78, 357; 260/396 R; 536/53

[56] References Cited

U.S. PATENT DOCUMENTS 4,377,570 3/1983 Durette et al. .................... 424/88

OTHER PUBLICATIONS

Dagani, "Efforts Intensify to Develop Drugs, Vaccines That Combat AIDS", C & E News, Dec. 8, 1986, pp. 7–14.

*Primary Examiner*—John Kight
*Assistant Examiner*—Nathan M. Nutter
*Attorney, Agent, or Firm*—Robert J. North; John W. Harbour

[57] ABSTRACT

Disclosed are specific dipeptidyl 4-0, 6-0-acyl-2-amino-2-deoxy-D-glucose derivatives which, either alone, or in combination with an anti-AIDS drug, e.g. azidothymidine, protect against opportunistic bacterial, fungal and viral infection in a human host immunocompromised by an AIDS-related virus, as well as help to suppress the AIDS-related virus itself.

3 Claims, No Drawings

DIPEPTIDYL 4-0-,6-0-ACYL-2-AMINO-2-DEOXY-D-GLUCOSE COMPOSITIONS AND METHODS OF USE IN AIDS-IMMUNOCOMPROMISED HUMAN HOSTS

BACKGROUND OF THE INVENTION:

1. Field of the Invention:

This invention relates to dipeptidyl 4-0, 6-0 acyl-2-amino 2 deoxy-D-glucoses which alone, or in combination with an anti AIDS drug, e.g. azidothymidine, protect against opportunistic, bacterial, fungal or viral infection in a human host, immunocompromised by an AIDS-related virus.

2. Brief Description of Disclosures in the Art

The search for new immunostimulants capable of augmenting host defenses to combat infection, cancer and congenital immunodeficiency disorders is an increasingly important area of pharmaceutical endeavor particularly as it relates to AIDS related viruses.

Seven years ago few had ever heard of acquired immune deficiency syndrome, or AIDS. This puzzling affliction, then seen in only a small number of young, homosexual men, was something new and unnamed. Today, it's hard to find anyone in the U.S. who hasn't heard of AIDS, the disease that can debilitate and then kill its victim with horrific swiftness.

AIDS has come to be recognized as a public health emergency. More than 27,700 American men, women, and children have been stricken by it; the death toll is 16,000 and rising. The U.S. Public Health Service predicts that by the end of 1991 more than 179,000 persons will have succumbed to the disease.

Thus far, there is no cure for AIDS.

Technically, acquired immune deficiency syndrome (AIDS) is a transmissible deficiency of cellular immunity characterized by opportunistic infections and certain rare malignancies. The dominant risk groups for AIDS include homosexually active males, intravenous drug abusers, recipients of transfusions and blood products, and the heterosexual partners and children of high-risk individuals, suggesting the involvement of an infectious agent transmitted through intimate contact or blood products.

Recent evidence indicates that the infectious agent responsible for disease transmission is a novel lymphotropic retrovirus, currently designated HIV I (human immunodeficiency virus) and also known as lymphadenopathy-associated virus (LAV) (Barré-Sinoussi et al., Science 220: 868 (1983)). Similar viruses have been reported by other scientific groups (Popovic et al., Science 224: 497 (1984); Levy et al. Science 225: 840 (1984)) and designated human T cell lymphotropic virus type III (HTLV-III), AIDS-associated retrovirus (ARV), or immune deficiency associated virus (IDAV). Still more recent data indicates that LAV, HTLV III, ARV and IDAV share several important characteristics, including substantial nucleotide homology (Wain-Hobson et al., Cell 40: 9 (1985); Muesing et al., Nature 313: 450 (1985); Sanchez-Pescador et al., Science 227: 484 (1985)), and should be considered isolates of the same virus, although there is a likelihood that strain to-strain variations among the viral isolates will exist. In addition to exhibiting substantial nucleotide homology, the isolates are similar with respect to morphology, cytopathology, requirements for optimum reverse transcriptase activity, and at least some antigenic properties (Levy, supra: Schupbach et al., Science 224: 503 (1984)).

The above materials are hereby incorporated by reference to characterize the phrase "AIDS-related virus".

U.S. Pat. No. 4,368,190 to Shen et al. (assigned to Merck & Co. Inc.) describes immunologically active depeptidyl 4-0, 6 0 acyl 2 amino 2-deoxy-D-glucoses described herein and their methods of preparation, which reference is hereby incorporated by reference for this particular purpose.

However, the above disclosure does not specifically describe the use of the compounds alone, or in combination with an anti AIDS drug, e.g. azidothymidine, for use as host resistance enhancing agents, i.e., immunostimulators, specifically to combat opportunistic viral, fungal, bacterial infections in AIDS-immunocompromised hosts.

SUMMARY OF THE INVENTION:

In accordance with the present invention there is provided a method for enhancing host resistance to opportunistic infection in a AIDS immunocompromised human host comprising the step of administering to said host a composition containing a compound of the formula (I):

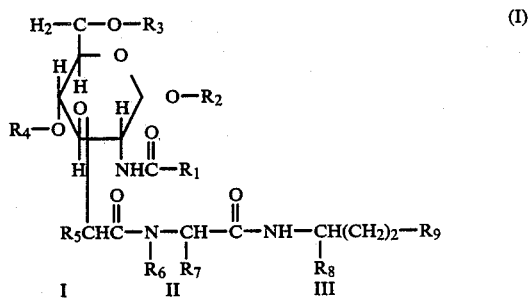

wherein:

$R_1$ is $C_{1-7}$ alkyl; $C_{1-7}$ alkyl substituted by hydroxy, mercapto, alkoxy of 1-3 carbons, alkyl mercapto of 1 3 carbons, hydroxy or mercapto esterfied by an acid of 1-4 carbon atoms, halogen, carboxyl, or carboxyl functionally modified by esterification with a lower alcohol of 1 3 carbons or by amidation; phenyl; or phenyl substituted by one or more alkyl groups of 1 3 carbon atoms or hydroxy or mercapto groups either free or etherified by an alkyl group of 1 3 carbons or esterified by an acid of 1-4 carbons, alkyldioxy of 1-4 carbons, cycloalkyldioxy of 5-7 carbon atoms, amino, or trifluoromethyl;

$R_2$ is hydrogen; $C_{1-7}$ alkyl; $C_{1-7}$ alkyl substituted by hydroxy, mercapto, alkoxy of 1-3 carbons, alkyl mercapto of 1-3 carbons, hydroxy mercapto esterified by an acid of 1-4 carbon atoms, halogen, carboxyl, or carboxyl functionally modified by esterification with a lower alcohol of 1-3 carbons or by amidation; phenyl; phenyl substituted by one or more alkyl groups of 1-3 carbon atoms or hydroxy or mercapto groups either free or etherified by an alkyl group of 1-3 carbons or esterified by an acid of 1-4 carbons, alkyldioxy of 1-4 carbons, cycloalkyldioxy of 5-7 carbon atoms, amino, or trifluoromethyl; phenyl $C_{1-4}$ alkyl; or phenyl $C_{1-4}$ alkyl substituted by one or more alkyl groups of 1-3 carbon atoms or hydroxy or mercapto groups either free or etherified by an alkyl group of 1-3 carbons or esterified by an acid of 1-4 carbons, alkyldioxy of 1-4 carbons, cycloalkyldioxy of 5-7 carbon atoms, amino, or trifluoromethyl;

$R_3$ and $R_4$ may be the same or different and are each independently hydrogen, provided that $R_3$ and $R_4$ may not both be hydrogen; or $R_3$ and $R_4$ may be the same or different and are each independently hydrogen, provided that $R_3$ and $R_4$ may not both be hydrogen; or

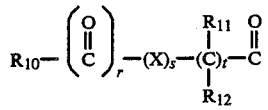

where X is —O—; —S—; or

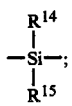

$R_{10}$ is hydrogen; $C_{1\text{-}30}$ alkyl; $C_{2\text{-}30}$ alkenyl; $C_{1\text{-}30}$ alkoxy; phenyl; Cphd 1-20 alkylsulfonyl; or cholesteryl;

$R_{11}$, $R_{12}$, and $R_{15}$ may be the same or different and are each independently hydrogen; $C_{1\text{-}20}$ alkyl; $C_{1\text{-}20}$ alkylcarbonyloxy; amino; benzyl; $C_{2\text{-}20}$ alkoxymethyl; $C_{1\text{-}20}$ alkylamido; or

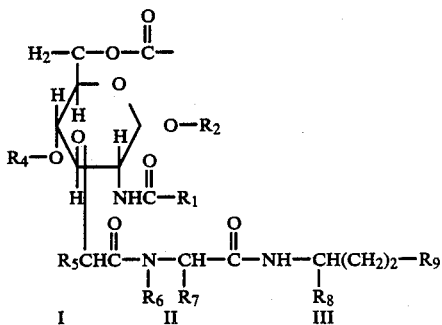

r is 0 or 1; s is 0 or 1; and t is 0 to 20; provided that s may only be 0 when both r and t are greater than 0 or when r is 0 and $R_{10}$ is amino; phenyl; substituted phenyl; 1-adamantyl; or heterocycle selected from the group consisting of 2- or 3- furyl, 2- or 3- thienyl, 2 or 3pyrrolidinyl, 2-, 3- or 4- pyridyl, and 1-tetrazolyl, said heterocycle optionally substituted with $C_{1\text{-}20}$ alkylcarbonyl; and where $R_3$ or $R_4$ is other than hydrogen, the other of $R_3$ or $R_4$ may additionally be $C_{1\text{-}4}$ alkylcarbonyl;

$R_5$ is hydrogen or $C_{1\text{-}7}$ alkyl;

$R_6$ is hydrogen or $R_6$ and $R_7$ taken together are $R_7$ is hydrogen; $C_{1\text{-}7}$ alkyl; hydroxymethyl; mercaptomethyl; benzyl; or substituted benzyl; and $R_9$ may be the same or different and are each independently COOR, or CONR'R", where R is hydrogen or $C_{1\text{-}7}$ alkyl, and R' and R" are hydrogen or $C_{1\text{-}3}$ alkyl; when $R_5$ is $C_{1\text{-}10}$ alkyl, the stereochemistry at asymmetric center I is D or L;

when $R_7$ is other than hydrogen, the stereochemistry at asymmetric center II is L; and the stereochemistry at asymmetric center III is D; and pharmaceutically acceptable acid addition and quaternary salts thereof; in a physiologically acceptable medium in an amount effective to impart resistance to viral, bacterial, fungal infection in an AIDS-immunocompromised human host.

Particularly preferred compounds of the composition are the following: 2-acetamido 6-0-behenoyloxyisobutyryl-2-deoxy-3O-(D-2-propionyl-L alanyl D-isoglutamine)-D-glucose 2-acetamido-2-deoxy-6-O-(N,O dipalmitoyl-D,L-seryl)-3O-(D-2-propionyl-L-alanyl-D-isoglutamine)-D-glucose 2-acetamido-6-O-(adamantane 1 carbonyl)-3-O-(D-2-propionyl-L-alanyl-D-isoglutamine)-D-glucose 2-acetamido-6-O-behenoyloxyacetyl-2 -deoxy-3-O-(D-2-propionyl-L-alanyl-D-isoglutamine)-D-glucose 2-acetamido-6-O-[d-2-(3-chloro-4-cyclohexylphenyl)-propionyl]-2-deoxy 3-O-(D-2-propionyl-L-alanyl-D-isoglutamine)-D-glucose 2-acetamido-2-deoxy-6-O-(N palmitoyl-L-prolyl)-3-O-(d-2-propionyl-L-alanyl-D-isoglutamine)-D-glucose 2-acetamido 2 deoxy-6-O-(2 methyl 2 N palmitoylamidopropionyl)-3-O-(D-2-propionyl-L-alanyl-D-isoglutamine)-D-glucose 2-acetamido-2-deoxy-6-O-(N-palmitoylglycyl)-3-O-(D-2-propionyl-L-alanyl-D-isoglutamine)-D-glucose 2-acetamido-2-deoxy 6-O-(N-palmitoyl-L-valyl)-3-O-(D-2-propionyl-L-alanyl-D-isoglutamine)-D-glucose 2-acetamido-2-deoxy-6-O-(N-palmitoyl-L-phenylalanyl)-3-O-(D-2-propionyl-L-alanyl-D-isoglutamine)-D-glucose 2-acetamido-2-deoxy 6-O-(N,O dihexadecyl D,L-seryl)-3-O-(D-2-propionyl-L-alanyl-D-isoglutamine)-D-glucose 2-acetamido-2-deoxy-6-O-(D,L-2 palmitamidopalmitoyl)-3-O-(D-2-propionyl-L-alanyl-D-isoglutamine)-D-glucose 2-acetamido-2 deoxy-6-O-(N,N'-dipalmitoyl-L-lysyl)-3-O-(D-2-propionyl-L-alanyl-D-isoglutamine)-D-glucose 2-acetamido-2-deoxy-6-O-(N-hexadecanesulfonylglycyl)-3-O-(D-2-propionyl-L-alanyl-D-isoglutamine)-D-glucose Bis(6-O-muramyl dipeptide)0 palmitoyltartronate 2-acetamido-6-O-cholesteryloxycarbonyl-2-deoxy-3-O-(D-2-propionyl-L-alanyl-D-isoglutamine)-D-glucose Methyl 2-acetamido 2-deoxy-6-O-hexadecyloxycarbonyl-3-O-(D-2-propionyl-L-alanyl-D-isoglutamine)-$\beta$-D-glucopyranoside Methyl 2 acetamido-6-O-behenoyloxyisobutyryl-2-deoxy-3-O-(D-2-propionyl-L-alanyl-D-isoglutamine)-$\beta$-D-glucopyranoside 2-acetamido-2-deoxy-6-O-(16-hydroxyhexadecanoyl)-3-O-(D-2-propionyl-L-alanyl-D-isoglutamine)-D-glucose 2-acetamido-6-O-(16 acetoxyhexadecanoyl)-4-O-acetyl-3-O-(D-2-propionyl-L-alanyl-D-isoglutamine)-D-glucose 2-acetamido-2-deoxy-6-O-(2-furoyl)-3-O-(D-2-propionyl-L-alanyl-D-isoglutamine)-D-glucose 2-acetamido-2-deoxy-4,6-di-O--methoxyacetyl-3-O-(D-2-propionyl-L-alanyl-D-isoglutamine)-D-glucose 2-acetamido-4,6-di-O-acetamidoacetyl-2-deoxy-3-O-(D-2-propionyl-L-alanyl-D-isoglutamine)-D-glucose 2-acetamido-2-deoxy-6-O-(5-ketohexanoyl)-3-O-(D-2-propionyl-L-alanyl-D-isoglutamine)-D-glucose 2-acetamido-6-O-(6-aminohexanoyl)-2-deoxy-3l-O-(D-2-propionyl-L-alanyl-D-isoglutamine)-D-glucose 2-acetamido-6-O-(6-acetamidohexanoyl)-2-deoxy-3-O-(D-2-propionyl-L-alanyl-D-isoglutamine)-D-glucose 2-acetamido-2-deoxy-6-O-(phenylacetyl)-3-O-(D-2-propionyl-L-alanyl-D-isoglutamine)-D-glucose 2-acetamido-2-deoxy-6-O-(phenoxyacetyl)-3-O-(D-2-propionyl-L-alanyl-D-isoglutamine)-D-glucose 2-acetamido-2-deoxy-6-O-(ethoxycarbonyl)-3O-(D-2-propionyl-L-alanyl-D-isoglutamine)-D-glucose 2-acetamido-2-deoxy-6-O-(1-tetrazolylacetyl)-3-O-(D-2-propionyl-L-alanyl-D-isoglutamine)-D-glucose Also provided is a composition containing the compound described above, in combination with an anti-AIDS drug, for enhancing the host resistance of a human AIDS-immunocompromised host.

Specifically provided is where the composition contains an anti AIDS drug selected from one or more of the following: azidothymidine, AL 721, ampligen, ansamycin, azimexon, cyclosporine, foscarnet, HPA 23, imreg 1, inosine pranobex, alpha interferon, interleukin 2, D penicillamine, ribavirin, suramin, CS 85, 2', 3'-dideoxycytidine, 2', 3'-dideoxyadenosine, gamma interferon, RNA deriv, Immune globulin IG IV, thymopentin, thymostimulin, methionine enkephalin or equivalents thereof.

Also provided is a method for enhancing resistance to opportunistic bacterial, fungal or viral infection in a human host immunocompromised by an AIDS related virus comprising administering to said host a pharmaceutical composition, as described above, in which method, the anti AIDS drug can be administered in combination, concurrently or separately, with the indicated compound.

DETAILED DESCRIPTION OF THE INVENTION AND PREFERRED EMBODIMENTS

The compositions described herein provide very high levels of protection against opportunistic infections in immunocompromised animals and humans.

By the term "AIDS related virus" is meant the commonly designated HIV series (human immuno deficiency virus) formerly called HTLV and LAV, and species thereof, as described above in the indicated incorporated references.

These compositions may be used prophylactically to protect immunosuppressed animals or patients against infection by opportunistic organisms. In human medicine, the market includes surgery patients, burn victims, cancer patients receiving chemotherapy, aplastic anemics, diabetics, and military recruits. In animal health, the primary potential use markets include major segments of the worldwide economic animal populations during stressful shipping, mixing, and early life adaptation periods.

By the term "immunostimulant", as used herein, is meant a material which can be employed to potentiate a non-specific immune response on the part of the host.

The composition of the present invention does not contain specific antigens per se. Rather, the composition contains only immunostimulants for producing a generalized and nonspecific immunological response on the part of the host, and further include acceptable salts, carriers, diluents, vehicles and the like for intravenous, subcutaneous or intraperitoneal administration.

Intermediates for the compounds of Formula I may be prepared by condensing, using conventional procedures, a protected compound of Formula II with a protected compound of Formula III.

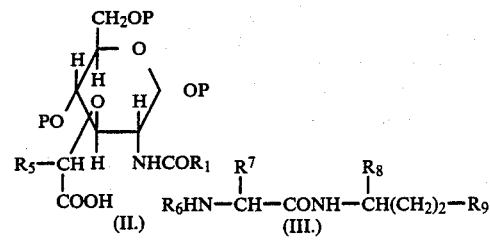

In the foregoing formulas, $R_1$, $R_5$, $R_6$, $R_7$, $R_8$ and $R_9$ represent the groups mentioned previously while P is a protecting group. The protecting group may be any suitable to protect the group to which it is attached during the condensation reaction and which may be readily removed thereafter. As protecting groups for the carboxyl group, there may be mentioned tertiary butyl, benzyl or benzhydryl. For the hydroxyl groups, there may be mentioned the acyl radical, for example, the alkanoyl radical, such as acetyl, the aroyl radical, such as benzoyl, and, in particular, radicals derived from carbonic acid, such as benzyloxycarbonyl or lower alkyloxycarbonyl. Also to be mentioned are alkyl radicals, such as tertiary-butyl, benzyl, nitrobenzyl, lower alkoxy radical, or the tetrahydropyranyl radical. In addition, there may be mentioned the optionally substituted alkylidene radicals that block the oxygen atoms at the C-4 and C 6 positions. Among the alkylidene radicals, one finds, in particular, the lower alkylidene radicals, especially ethylidene, isopropylidene, or propylidene, and also, the optionally substituted benzylidene radical, preferentially substituted at the para position. For a more complete listing of protecting groups, reference may be had to ,standard works on peptide chemistry, e.g. Bodanszsky et al., *Peptide Synthesis*, Chapter 4, Interscience Publishers, (1966), or Schroeder et al., *The Peptides* Vol. I, pp. xxiii xxix, Academic Press, (1965), and to the text *Protective Groups in Organic Chemistry*, Plenum Press, (1973), J. F. W. McOmie, (ed.).

The condensation is effected by reacting the compound II in the form where the carboxylic acid is activated with the amino compound III. The activated carboxyl group may be, for example, an acid anhydride, preferably, a mixed acid anhydride like an acetate of the acid, an amide of the acid like an imidazolid, an isoxazolid or an activated ester. The activated esters, include the cyanomethyl ester, the carboxymethyl ester, the p-nitrophenyl thioester, the p-nitrophenyl ester, the 2,4,5 trichlorophenyl ester, the pentachlorophenyl ester, the N-hydroxysuccinimide ester, the N hydroxyphthalimide ester, the 8 hydroxyquinoline ester. the 2 hydroxy 1,2 dihydro 1 carboethoxyquinoline esters, the N hydroxy piperidine ester or enol ester derived from N ethyl-5 phenylisoxazolium 3' sulfonate. The activated esters may equally be obtained from a carbodiimide by addition of N hydroxysuccinimide or from a substituted 1-hydroxybenzotriazole, for example, a halogen, methyl, or methoxy-substituted 3 hydroxy-4-oxo-3,4 dihydrobenzo[d]1,2,3 triazine.

The amino group may be activated, for example, by reaction with a phosphitamide.

Among the methods of reaction with the activated esters, one must mention in particular those that involve N ethyl 5 phenyl-isoxazolium-3' sulfonate (Woodward's Reagent K , N ethoxycarbonyl-2 ethoxy 1,2 dihydroquinoline, or carbodiimide. Upon completion of the coupling reaction, the protecting groups may be removed in conventional manner to yield a compound from which a compound of Formula I may be prepared.

The starting materials utilized are known or can be made in a known fashion. Thus, one can obtain compounds of Formula II, for example, by reacting the corresponding sugar unsubstituted at position-3 with a halogen-$R_5$-acetic acid where $R_5$ has the meaning mentioned above. The ether is obtained in the presence of a strong base. The halogen is preferentially bromo or chloro.

Another process of synthesizing intermediates for the compounds of Formula I consists of condensation and eventual deblocking in conventional manner of the protecting groups present in a compound of Formula IV.

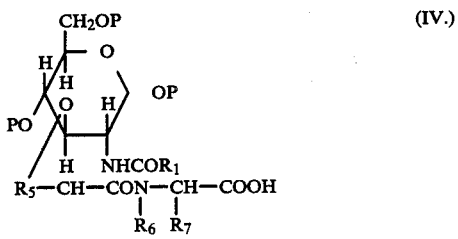

wherein $R_1$, $R_5$, $R_6$, and $R_7$ and P have the meaning mentioned above, with a compound of Formula V,

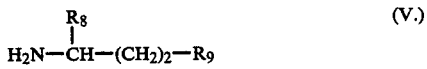

wherein $R_8$ and $R_9$ have the meaning mentioned above.

The condensation may be effected by reacting compound IV in the form of an activated carboxylic acid with the amino compound V or by reacting IV in the form of the free C terminal carboxyl group with compound V where the amino group is present in activated form. The activated carboxyl group can be, for example, an acid anhydride and preferably a mixed acid anhydride, an acid amide or an activated ester. Among these, one finds in particular the acid anhydrides, the amides, or the esters mentioned above. The amino group may be activated, for example, by reaction with a phosphitamide. The readily removable protecting groups correspond to those mentioned above.

The starting materials are obtained in classical fashion. One can, therefore, react the corresponding sugar unsubstituted at position 3 with halogen $R_5$-acetamido $R_7$ acetic acid or a compound of Formula II with an amino-$R_7$-acetic acid where the carboxyl group is blocked as mentioned above followed by removal of the protecting groups.

Another process for inserting the side chain at position-3 of the sugar radical consists in reacting a compound having structure VI

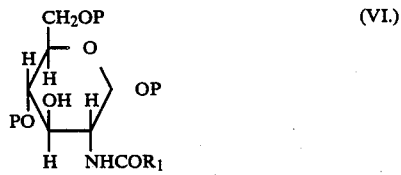

where $R_1$ and P have the signification mentioned above with a compound of Formula VII

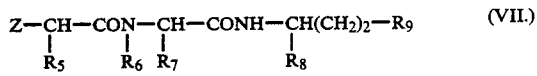

where Z represents an esterified hydroxy group capable of reacting and wherein $R_5$, $R_6$, $R_7$, $R_8$ and $R_9$ have the meaning given above followed by removal of the protecting groups optionally present. An esterified hydroxy group capable of reacting is, first of all, a hydroxy group esterified with a strong inorganic or organic acid and especially a group esterified by the hydrohalic acids, like hydrochloric acid, hydrobromic acid, or hydroiodic acid. The protecting groups correspond to those already mentioned above. One can remove them in a classical fashion, for example, by hydrogenolysis with hydrogen in the presence of a noble metal catalyst, such as palladium or platinum, or by acid hydrolysis. The starting materials utilized in this preparative route are known.

One can also obtain the intermediates for the compounds of Formula I by acid hydrolysis of the oxazoline and dioxalane rings in the compound of Formula VIII,

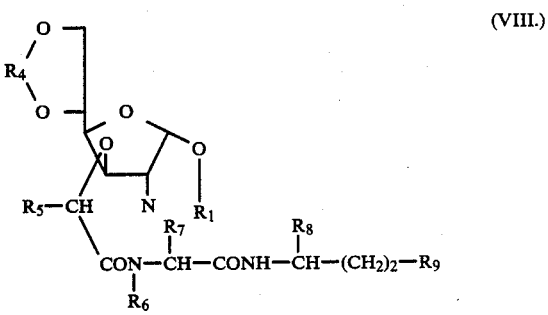

where $R_1$, $R_5$, $R_6$, $R_7$, $R_8$ and $R_9$ have the meaning mentioned above and where $R_\alpha$ is an alkylidene or cycloalkylidene group, and by removing the protecting groups optionally present.

Alkylidene signifies, particularly in this case, a lower alkylidene, such as isopropylidene and cycloalkylidene, especially cyclopentylidene or cyclohexylidene. This hydrolysis is effected egually in a classical fashion, for example, with acidic ion exchange resins, in particular, with an exchange resin containing sulfonic acid groups like Amberlite IR-120, (resins of styrene containing strongly acidic sulfonyl groups) or Dowex-50 (polystyrene sulfonic acids) or with a strong inorganic or organic acid like hydrochloric acid, hydrobromic acid, sulfuric acid or a sulfonic acid like methanesulfonic acid or a phenylsulfonic acid optionally substituted in its aromatic nucleus, like p-toluenesulfonic acid, or trifluoroacetic acid.

In the presence of water, one obtains at position 1 a free hydroxy group. In the presence of an alcohol of formula R2OH, where $R_2$ represents an optionally substituted alkyl group, one obtains the corresponding $R_2$ substituted compound. If one of the $R_8$ or $R_9$ carboxyl protecting groups P is the moiety resulting from esterifying the carboxyl group with an alcohol, in particular by a lower alcohol, the alcohol may be hydrolyzed, particularly at high temperature, with agueous acid to liberate the free acid. During this hydrolysis it is possible that the amino group at position 2 of the molecule of the sugar may be liberated. One must in this case lastly insert the group

This is achieved in the usual fashion by acylation. In the resulting compounds, the protecting groups may be removed from the peptide radical, for example, by hydrogenolysis, such as with activated hydrogen in a catalytic fashion, or by hydrolysis. The starting materials utilized here are obtained, for example, by inserting the radical $R_5$-acetamidopeptide in one or several steps in the corresponding oxazoline with a free hydroxy group at position 3 of the sugar radical.

Compounds wherein $R_7$ is other than methyl, may be obtained when, for example, one of the following amino acids is substituted for alanine:

| Amino acid | $R_7$ |
|---|---|
| serine | $CH_2OH$ |
| cysteine | $CH_2SH$ |
| phenylalanine | benzyl |
| tyrosine | p-hydroxybenzyl |
| valine | isopropyl |
| leucine | 2-methylpropyl |
| isoleucine | 1-methylpropyl |
| α-aminobutyric | $CH_2CH_3$ |
| norvaline | $CH_2CH_2CH_3$ |
| norleucine | $CH_2CH_2CH_2CH_3$ |

Compounds wherein $R_6$ and $R_7$ together are —$CH_2CH_2CH_2$ are obtained by substituting proline for alanine.

The term "substituted alkyl" for $R_1$ and $R_2$ refers to an alkyl group of from 1 to 7 carbon atoms substituted by hydroxy, mercapto, alkoxy of 13 carbons, alkyl mercapto of 13 carbons, hydroxy or mercapto esterified by an acid of 1-4 carbon atoms, halogen (F, Cl or Br), carboxyl, or carboxyl functionally modified by esterification with a lower alcohol of 1 3 carbons or by amidation. Preferably the alkyl substituents are hydroxy or mercapto, either free or substituted by an alkyl group of 1-3 carbons.

The substituents in the terms "substituted phenyl" for $R_1$ and $R_2$ or "substituted phenyl $C_{1-4}$ alkyl" for $R_2$ refer to the phenyl group substituted by one or more alkyl groups of 1-3 carbon carbons or hydroxy or mercapto groups either free, or etherified by an alkyl group of 1-3 carbons or esterified by an acid of 1-4 carbons, lower (1-4C) alkyldioxy, cycloalkyldioxy of 5-7 carbon atoms, amino, or trifluoromethyl.

The substituents in the term "substituted phenyl" for $R_{10}$, are halo and phenyl.

Compounds wherein $R_2$ is hydrogen and $R_1$ l is other than methyl are obtained by reacting 2-amino-2-deoxy-D-glucose, in the case where $R_1$ is alkyl or substituted-alkyl, with the appropriate alkanoic anhydride or alkanoyl halide, preferably chloride, or substituted alkanoic anhydride or substituted alkanoyl halide, preferably chloride, and in the case where R is phenyl or substituted-phenyl, with the appropriate aroic anhydride or aroyl halide, preferably chloride, or substituted aroic anhydride or substituted aroyl halide, preferably chloride, in the presence of an appropriate acid acceptor, such as pyridine or triethylamine. The protecting groups P are then introduced at the C-1, C-4, and C-6 positions to give a compound of Formula VI which may then be converted to a compound of Formula II or Formula IV.

In general, compounds wherein $R_2$ is other than hydrogen are prepared by reacting an alcohol of formula $R_2OH$ with the N alkanoylglucosamine or N aroylglucosamine to give the corresponding alkyl, substituted alkyl, phenyl, substituted phenyl, phenyl $C_{1-4}$ alkyl, or substituted phenyl $C_{1-4}$ alkyl glucopyranoside. The latter are then treated to block the C-4 and C-6 hydroxyl groups, for example, as benzylidene acetal, by reaction with benzyladehyde and boron trifluoride etherate or zinc chloride. The blocked $R_5$-acetamidodipeptide fragment is then inserted into the blocked glucopyranoside having a free hydroxyl group at position -3 of the sugar radical in one or several steps as described above. The protecting groups are then removed by hydrogenolysis with hydrogen in the presence of a noble metal catalyst, or by acid hydrolysis.

For $R_8$ and $R_9$, among the optionally esterified carboxyl groups can be mentioned the carboxyl group esterified by a lower alcohol of 1-3 carbons, like methanol or ethanol. The carboxyl group can also be amidated, unsubstituted at the nitrogen atom or mono or di substituted with an alkyl, in particular, a lower alkyl, an aryl, particularly phenyl, or an aralkyl, particularly benzyl.

Most preferably, $R_2$ is H, alkyl of 1-3 carbons, benzyl, phenyl or phenyl p substituted by alkyl (1-3C), amino, halogen, hydroxy or trifluoromethyl; $R_1$ is alkyl of 1-3 carbons, or phenyl, or phenyl p-substituted by alkyl (1-3C), amino, halogen, hydroxy or trifluoromethyl, $R_5$ is H or lower alkyl of 1-3 carbon; $R_7$ is H, alkyl of 1-4 carbons, hydroxymethyl, mercaptomethyl, benzyl or p-hydroxybenzyl; $R_6$ and $R_7$ together are —$CH_2CH_2CH_2$—; and $R_8$ and $R_9$ are carboxyl, carboxyl esterified by an alcohol of 1-4 carbons, carboxamide, or monoalkyl or dialkyl substituted carboxamide wherein the alkyl group has from 1-3 carbons.

The compounds of Formula I are prepared by reaction of the intermediates described above with the appropriate acid derivative whereby condensation results in the desired 6-O- and/or 4-O- substituted compounds. All of the appropriate acids for preparing the compounds of Formula I are known compounds or may be prepared by known methods in an obvious manner. The condensation reaction will take place preferentially at the 6 position of the glucose ring, thus giving predominantly or exclusively 6-O- derivatives under normal reaction conditions. When the reaction conditions are driven, 4-O- derivatives can also be obtained, giving 6-O- and 4-O- derivatives. Where it is desired to prepare only 4-O- derivatives, the 6 position must be blocked while the 4 position substitution takes place, followed by deblocking. The blocking and deblocking reactions may be carried out in accordance with procedures well known in the art.

The condensation reactions may be carried out in accordance with procedures well established in the art for preparing organic compounds. Thus, the condensation may be carried out using the carboxylic acid, the acid anhydride, or the acid halide.

Where the carboxylic acid is utilized, a coupling agent, for example N,N dicyclohexyl carbodiimide (DCC), or 4 dimethylaminopyridine (DMAP), will be employed. The reaction is carried out in an inert aprotic solvent, such as dimethyl formamide, dimethylsulfoxide, or pyridine, at a temperature of from 0° to 50° C. for from 6 hours to 6 days.

Where the acid anhydride is utilized, a coupling agent may be employed, although this is not necessary. However, an acid acceptor, such as pyridine or trimethylamine, should be used. The solvent medium in which the reaction is carried out and the other reaction conditions are the same as for the carboxylic acid condensation.

Where the acid halide is utilized, all of the reaction conditions are the same as those for the acid anhydride condensation.

Once the condensation reaction has been completed, the remaining protecting groups are readily removed by hydrogenolysis, preferably carried out with a catalyst such as palladium oxide in the presence of glacial acetic acid.

The obtained compounds can be transformed to their salts in a classical fashion, for example, by reacting the acidic compounds obtained with alkaline or alkaline earth hydroxides, or the basic compounds with acids.

The Formula I compounds can be used in the form of salts derived from inorganic or organic acids. Included among such salts are the following: acetate, adipate alginate, aspartate, benzoate, benzenesulfonate, bisulfate, butyrate, citrate, camphorate, camphorsulfonate, cyclopentanepropionate, igluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, succinate, tartrate, thiocyanate, tosylate, and undecanoate. Also, the basic nitrogen containing groups can be guaternized with such agents as lower alkyl halides, such as methyl, ethyl, propyl, and butyl chloride, bromides and iodides; dialkyl sulfates like dimethyl, diethyl, dibutyl, and diamyl sulfates; long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds in the present invention possess immunostimulatory properties and may be used as immunomodulating agents, i.e. to stimulate the host immune response. They are especially useful for increasing the host response against viral infections.

The pharmaceutically acceptable compounds of the present invention can be used, for example, for the manufacture of pharmaceutical preparations that contain a pharmaceutically effective amount, for example an amount sufficient for immunostimulation, of the active ingredient together or in admixture with a significant amount of inorganic or organic, solid or liquid pharmaceutically acceptable carriers.

The pharmaceutical preparations according to the invention are for enteral, such as oral or rectal, and parenteral, such as intraperitoneal, intramuscular or intravenous, administration to warm blooded animals and contain the pharmacological active ingredient alone or together with a pharmaceutically acceptable carrier.

The carriers may be inorganic or organic and solid or liquid. For example, there are used tablets or gelatine capsules that contain the active ingredient together with diluents, for example lactose, dextrose, sucrose, mannitol, sorbitol, cellulose and/or glycerine, and/or lubricants, for example silica, talc, stearic acid or salts thereof, such as magnesium or calcium stearate, and/or poly ethylene glycol. Tablets may also contain binders, for example magnesium aluminium silicate, starches, such as corn, wheat or rice starch, gelatine, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, colorings, flavorings and sweeteners. The pharmacologically active compounds of the present invention can also be used in the form of parenterally administrable preparations or in the form of infusion solutions. Such solutions are preferably isotonic agueous solutions or suspensions, it being possible, for example in the case of lyophilized preparations that contain the active ingredient alone or together with a carrier, for example mannitol, for these to be manufactured before use. The mentioned solutions or suspensions may contain viscosity-increasing substances, such as sodium carboxymethylcellulose, carboxymethylcellulose, dextran, polyvinylpyrrolidone or gelatine. The pharmaceutical preparations may be sterilized and/or contain adjuncts, for example preservatives, stabilizers, wetting agents and/or emulsifiers, solubilizers, salts for regulating the osmotic pressure and/or buffers. The present pharmaceutical preparations which, if desired, may contain other pharmacologically active ingredients, such as antibiotics, are manufactured in a manner known per se, for example by means of conventional mixing, granulating, confectioning, dissolving or lyophilizing processes, and contain approximately from 0.001% to 99%, especially from approximately 0.01% to approximately 10%, more especially from 0.1% to 5%, of the active ingredient(s), an active ingredient concentration of less than 1% being especially suitable for preparations that are to be applied topically.

Pharmaceutical preparations according to the invention may be, for example, in dosage unit form, such as dragees, tablets, capsules, suppositories or ampoules.

Pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragee cores. It is also possible to incorporate them into synthetic carriers that release the active ingredients, or allow them to diffuse, in a controlled manner.

The manufacture of injection preparations is carried out in customary manner under antimicrobial conditions, as is the filling into ampoules or phials and the sealing of the containers.

Furthermore, the compounds of the present invention provide, alone or in combination with "anti-AIDS drugs", human host protection against opportunistic infections in individuals immunocompromised by an AIDS related infectious organisms, as well as a direct therapeutic effect on the AIDS related virus itself. These include fungal, viral and bacterial, including the specific conditions of Kaposi s sarcoma and pneumocystis pneumonia. They are also capable of potentiating antibiotic activity.

By the term "anti-AIDS drugs" is meant therapeutic drugs which are thought to act directly or indirectly against the AIDS-related virus by a variety of known or unknown mechanisms.

The following anti AIDS drugs are currently being investigated and are known to exhibit either some antiviral or immunomodulating effect in a human host against the AIDS related virus (from *Chemical & Enginineering News,* Dec. 8, 1986, pp 7–14, hereby incorporated by reference for this purpose):

AL 721. Lipid mixture composed of neutral glycerides, phosphatidylcholine, and phosphatidylethanolamine in 7:2:1 ratio. Interferes with HIV infectivity but not by inhibiting reverse transcriptase; possibly it disrupts the virus's membrane. No adverse effects observed during a six week clinical trial.

Ampligen. Mismatched double-stranded RNA polynucleotide that induces the body to release interferon, thus stimulating antiviral activity. Reportedly does not have side effects of interferon injections. Currently undergoing preliminary clinical trials in AIDS patients.

Ansamycin (rifabutin, $C_{45}H_{29}N_4O_{11}$). Italian antibacterial drug, a member of the rifamycin group of antibiotics, which are characterized by a natural ansa structure (chromophoric naphthohydroquinone group spanned by a long aliphatic bridge). Drug has shown some efficacy in treating AIDS patients with an opportunistic infection caused by the bacterium *Mycobacterium avium intracellulare.*

Azidothymidine (AZT, 3' azido 3'-deoxythymidine zidovudine). First drug to show promise in prolonging lives of patients with AIDS or AIDS-related complex (ARC). Well absorbed orally and effectively penetrates central nervous system, but has relatively short half-life in the body and some toxicity, with anemia and headaches. ARC patients treated with AZT showed virtually no toxic effects.

Azimexon. Cyanaziridinyl immunemodulator. Early trial showed improvements in symptoms and immune function in patients with ARC but not AIDS; only toxic effect was mild hemolysis (disintegration of red blood cells with release of hemoglobin), which disappeared when treatment ceased.

Cyclosporine (cyclosporin A). Cyclic undecapeptide with potent immunosuppressive effects, used in cancer therapy. Inhibits T4 lymphocyte-dependent immune responses. Basis of controversial AIDS therapy in France; rationale is that HIV infects "activated" T4 cells, which are primed to defend the body, so drug that prevents activation of T4 cells may limit progression of disease. The French claim encouraging results with it.

Foscarnet (trisodium phosphonoformate). Swedish drug that has been used to treat CMV infection in immunocompromised patients, also to treat herpes. Inhibits HIV reverse transcriptase activity in vitro at levels pharmacologically acceptable in vivo. Formulation problems and serious side effects have been encountered. No results yet reported in HIV infected patients.

HPA-23 (ammonium 21 tungsto 9 antimoniate, $[(NH_4)_{18}(NaW_{21}So_9O_{86})_{17}]$. Inhibits reverse transcriptase in several retroviruses in vitro, but mechanism of antiviral action against HIV is unknown. Drug has shown some tendency to check the growth of HIV, but no therapeutic benefit has been documented in AIDS patients.

Imreg 1. Proprietary immunemodulator derived from white blood cells. Reportedly can enhance production of other biological response modifiers such as interleukin-2 and γ-interferon. which are critical to normal functioning of immune system.

Inosine granobex (isoprinosine, inosiplex). p-Acetamidobenzoic acid salt of (1 dimethylamino 2 propanol:inosinate complex 3:3:1 molar ratio). Chemically synthesized antiviral and immunemodulator originally developed to enhance memory in elderly. In one study, found to improve immune function in ARC patients.

α-Interferon. Glycoprotein produced by cells in response to virus infection; helps amplify or regulate immune responses. Checks the growth of HIV in vitro. Has induced tumor regression in some AIDS-related Kaposi's sarcoma cases. Not known whether α-interferon has anti HIV activity in vivo.

Interleukin-2 (IL-2). Protein made by white blood cells that mediates production of interferon. Inability to produce IL-2 may predispose AIDS patients to opportunistic infections. Preliminary results of therapy with recombinant IL-2 not encouraging, but trials continue.

D Penicillamine (3-mercapto D valine). Used to treat rheumatoid arthritis and Wilson's disease, a rare copper storage disease. Inhibits HIV reproduction in humans. In trials at George Washington University Medical Center, it suppressed the virus but also temporarily depressed T cell levels in 13 AIDS patients with perpetually swollen glands.

Ribavirin (1 8 D ribofuranosyl-1,2,4-triazole-3-carboxamide). Synthetic nucleoside used to treat a viral respiratory infection in children. In early clinical trials, it inhibited viral replication and improved immune function in AIDS patients. Longer (24-week) trial in 373 ARC patients has been completed; at 12 weeks, ribavirin's safety profile was judged to be acceptable, and the drug was found to be well tolerated.

Suramin ($C_{51}H_{34}Na_6O_{23}S_6$). Antiparasitic agent. Potent inhibitor of HIV reverse transcriptase, but also significantly inhibits desirable biological functions. In AIDS patients, it has produced little or no evidence of clinical improvement or immunologic recovery. Has serious side effects, inability to penetrate central nervous system. Not considered appropriate for single-agent use in AIDS. No longer being actively pursued.

Furthermore, the US Food and Drug Administration has released a list of 16 proposed AIDS treatments which have received IND status. The list contains only treatments which "have been publicly acknowledged by their sponsors", and therefore some experimental treatments may have been omitted.

| Experimental treatment | Sponsor |
|---|---|
| Immunomodulators | |
| Thymopentin | Ortho Pharmaceuticals |
| Thymostimulin | Serono Laboratories |
| Methionine-enkephalin | National Jewish Hospital |
| Isoprinosine | Newport Pharmaceuticals |
| Antivirals | |
| Ansamycin | Adria Laboratories |
| Ribavirin | Viratek/ICN Pharmaceuticals |
| Dideoxycytidine (DDC) | National Cancer Institute |
| HPA-23 | Rhone-Poulenc |
| AL-721 | Matrix Laboratories[1] |
| Foscarnet | National Institute of Allergy and Infectious Diseases |
| Biologicals | |
| Alpha-interferon | Hoffmann-La Roche |
| Gamma-interferon | Genentech |
| Imreg-1 | Imreg Inc |
| Interleukin-2 | Hoffmann-La Roche |
| RNA deriv | HEM Research |

| Experimental treatment | Sponsor |
|---|---|
| Immune globulin IG-IV | Sandoz Pharmaceuticals and Alpha Therapeutics |

Further, Yakult's immunostimulant, LC 9018, and two herbal products, shosaikoto and ginseng, being studied by Tsumura Juntendo, may be of benefit in patients with AIDS.

LC-9018 has been found to be about 20 times more potent than Ajinomoto's lentinan in inducing macrophage activation, and it is undergoing clinical trials in AIDS patients in the US. Phase III trials with LC-9018 in patients with cancer are currently underway in Japan. Shosaikoto and ginseng have been found to increase depleted helper T cell counts in seven of nine AIDS-carriers studied by researchers at Tsumura Juntendo and Tokyo Medical University.

Furthermore, HEM Research's potential anticancer agent, ampligen (a mismatched double stranded RNA), reduces at least five fold the concentration of Wellcome's azidothymidine (Retrovir) required for inhibitory activity against human immunodeficiency virus (HIV) in vitro, (*The Lancet* Apr. 18th, p. 890). Ampligen is currently in Phase II clinical trials as an anticancer agent and HEM is seeking partners to fund a clinical trial in AIDS.

At higher concentrations of azidothymidine, there seemed to be a synergistic relation between the two compounds, since complete protection was provided by combined suboptimal doses of each drug. Ampligen could reduce the dose of azidothymidine required for a therapeutic effect in vivo, so reducing its toxicity.

Since the two drugs have entirely different modes of action, it is unlikely that they will exert toxicities other than those associated with each drug alone. In recent clinical studies, "virtually no toxicity" was associated with intravenous ampligen. Moreover, since ampligen has clinically demonstrated immunological as well as antiviral activity, its use together with azidothymidine may have pronounced and long-term beneficial effects on the course of AIDS beyond that which can be estimated in vitro.

In addition, CS 85, or 3' azido 2', 3'-dideoxy-5-ethyl-(uridine), developed by Raymond F. Schinozi at the Veterans Administration Medical Center and Emory University, both in Atlanta, Georgia, shows promise.

All of the above described compounds are deemed to be included within the scope of the term "anti-AIDS drug" as used herein. Use of more than one of these compounds, in addition to the glyco peptide of structure I, in the combination composition is contemplated.

The composition containing the glycopeptide compounds and an above described anti AIDS drug will contain the glycopeptide in an amount as described above and the anti-AIDS drug in an amount, based on the glycopeptide, in a weight ratio of 1:3 to 3:1 and preferably 1:1 based on the weight of glycopeptide.

The dosage form of the combination drug will be 1 to 50 mg/kg of human body weight per day and preferably 2.5 to 40 mg/kg.

The method of co administering the two ingredients, if not using the combination composition can be separately, concurrently or simultaneously.

The present invention is also directed to pharmaceutical preparations that contain a compound of Formula I. Among the pharmaceutical preparations relevant to this invention are salts that are administered by external route, for example, orally, rectally or parenterally to human species. Preparations may be administered that contain the pharmacologically active compound by itself or mixed with a pharmacologically acceptable carrier. The dose of the pharmacologically active compound depends on the sex, the age, and the state of the human individual and the mode of application.

The new pharmaceutical preparations contain from about 10% to about 95% and, preferably from about 20% to about 90% of a compound of the present invention. The pharmaceutical preparation relevant to this invention can be presented, for example, in the form of unit doses like tablets, capsules, suppositories, and ampoules.

Also a subject of the invention is a method for administering to an immunocompromised host a composition as described herein, containing a compound of the formula I, as described, contained in a suitable carrier which may or may not have additional material such as diluents and other materials which may be deemed necessary under the circumstances. However, it is understood that the immunostimulatory preparation does not in fact include a specific antigen as a composition component.

The following examples exhibit the subject invention as contemplated by us and should not be construed as being limiting with respect to the scope and nature of the instant invention.

The immunostimulatory properties of the compounds in the present invention can be demonstrated with the following protocols:

1. In vivo Stimulation of Humoral Response: Increase in the Production of Antibodies Against Bovine Serum Albumin (BSA) in the Mouse Mice (NMRI) are immunized by i.p. injections of 10 mg of BSA without precipitate. At 0, 9, 15 and 29 days later blood samples are taken and analyzed for anti-BSA antibody titers by the passive hemagglutination technique. At the dose utilized, soluble BSA is subimmunogenic for the receiving animals, that is, it does not cause any antibody production, or at most a completely insignificant production. Additional treatment of the mice with certain immunostimulants before or after administration of antigen leads to an increase in antibody titer in the serum. The effect of the treatment is expressed by the obtained score, that is, the sum of the logs to the base 2 of the differences of the titer at 3 days of bleeding.

The compounds of the present invention are capable of augmenting in a significant manner the production of anti-BSA antibodies by i.p. or subcutaneous application (s.c.) of 100–300 mg/kg/animal during 5 consecutive days (day 0 to day 4) after immunization with BSA.

The immunostimulatory effect of the compounds mentioned herein depend on the antigen, contrary to other bacterial immunostimulants (like LPS of *E. coli*). The injection of the compounds of the present invention results in augmentation of anti-BSA antibody titer only in mice immunized with BSA, and not with non-immunized mice. Subcutaneous administration is as efficacious as i.p., that is, the immunostimulatory effect observed is systemic and does not depend on the fact that the stimulant Was administered by the same route as the antigen or mixed with it, as is the case with classical adjuvants.

The compounds of the present invention permit specific augmentation of humoral immunity, improve immune response, and provide long-lasting immunostimulatory effects on systemic activation of immune apparatus.

2. Stimulation of Mitotic Responses of Lymphocyte Cultures

Mouse lymphoid cells are cultured in microtiter plates, in RPMI-1640 medium with 2% fetal calf serum. Cultures are set in triplicates and consist of $3-5\times10^5$ spleen or $1.5\times10^6$ thymus cells per well in a final volume of 0.2 ml. Class specific nitrogens are added at optimal or suboptimal concentrations, while control cultures are incubated without nitrogens. The tested compounds are added shortly after the nitrogens and the cultures are incubated for 48 hours at 37° with 5% $CO_2$. Incorporation of tritiated thymidine is determined after a pulse (1.0 µCi/well) during the last 6 hours in culture. The data are recorded as mean cpm and the effects of the compounds are presented as stimulation index (mean cpm in cultures with the compound/mean cpm in control).

The compounds of the present invention enhance the levels of thymidine incorporation in lymphocyte cultures, with or without mitogens. The stimulation indices are maximal in control cultures or in those with suboptimal doses of mitogens. Similar effects of the compound are provoked in cultures of different lymphocyte populations, namely, B cells (nude spleen), T cells (thymus) or their mixtures (normal spleen). The effects of the compounds are dose dependent. These compounds, therefore, are capable of stimulating proliferation of lymphocytes that participate in the humoral response (B cells) as well as in cellular immunity (T cells).

3. Compatibility

Although the compounds of the present invention produce their stimulatory effect with guinea pigs, for example, beginning with a single dose of 0.05 mg/kg s.c., and with mice after 5 applications of 10 mg/kg s.c., no toxic effect is observed after 5 applications of 300 mg/kg i.p., with the mouse. These compounds possess, therefore, a remarkable therapeutic index.

The compounds of the present invention thus have the capacity by systemic application, of increasing the immunological reactivity of the treated organism. Moreover, these compounds can enhance cellular as well as humoral immunity and activate lymphocytes responsible for the formation of antibodies.

The compounds of the present invention can consequently be employed as protective agents against infections caused by bacteria, viruses or pathogenic parasites, owing to immunity by humoral antibodies and/or to cellular mediation. These compounds are therefore especially indicated for stimulation of individual immune defense, e.g., at the time of chronic or acute infections or in cases of selective (antigen specific) immunological deficiencies as well as in situations of immunedeficiency, but also acquired general deficiency (i.e., not antigen-specific) as appears with age, during initial shock from a grave illness, and before and soon after radiation therapy or immunosuppressive hormones. The said compounds can subsequently be administered in combination with anti infectious antibiotics, chemical therapeutics or other methods of treatment, to combat immunological deficiencies. The described compounds are thus indicated equally for general prophylaxis of infectious disease in man and animal.

EXAMPLE 1

Preparation of 2-acetamido-6-O-behenoyloxyisobutyryl-2-deoxy-3-O-(D-2-propionyl-L-alanyl-D-glutamine)-D-glucose Step A: Preparation of benzyl-2-acetamido-6-O-behenoyloxyisobutyryl-2-deoxy-3-O-(D-2-propionyl-L-alanyl-D-isoglutamine benzyl ester)-a-D-glucopyranoside To benzyl-2-acetamido-2-deoxy-3-O-(D-2-propionyl-L-alanyl-D-isoglutamine benzyl ester)-α-D-glucopyranoside (0,447 mmol) was added dimethylformamide (4 ml.), behenoyloxyisobutyric acid (0.50 mmol), then dichloromethane (6 ml.), N,N'-dicylclohexylcarbodiimide (0.50 mmol) and 4-dimethyl aminopyridine (0.50 mmol). The mixture was stirred for 4 days at room temperature. The mixture was added to dichloromethane, washed with water and the product purified by preparative thin layer chromatography (silica) using chloroform/methanol/water: 85/15/1.5.

Step B: Preparation of 2-acetamido-6-O-behenoyloxyisobutyryl-2-deoxy-3-O-(D-2-propionyl-L-alanyl-D-isoglutamine)-D-glucose To benzyl-2-acetamido-6-O-behenoyloxyisobutyryl-2-deoxy-3-O-(D-2-propionyl-L-alanyl D-isoglutamine benzyl ester)-α-D-glucopyranoside (0.218 mmol) was added acetic acid (5 ml.) and palladium oxide (210 mg.). This mixture was shaken in a hydrogen atmosphere for 2 days. The solvent was removed in vacuo and the product purified by preparative thin layer chromatography (silica) using chloroform/methanol/water: 80/20/2.

EXAMPLE 2

Preparation of 2-acetamido-2-deoxy-6-O-(N,O-dipalmitoyl-D,L-seryl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of N,O-dipalmitoyl-D,L-serine, there are prepared in sequence, Step A: Benzyl-2-acetamido-2-deoxy-6-O-(N,O-dipalmitoyl-D,L-seryl)-3-O-(D-2-propionyl-L-alanyl-D-isogluamine benzyl ester)-a-D-glucopyranoside Step B: 2-Acetamido-2-deoxy-6-O-(N,O-dipalmitoyl-D,L-seryl)-3-O-(D-2-propionyl-alanyl-D-isoglutamine)-D-glucose

EXAMPLE 3

Preparation of 2-acetamido-6-O-(adamantane-1-carboxyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of adamantane-1-carboxylic acid, there are prepared in sequence, Step A: Benzyl-2-acetamido-2-deoxy-6-O-(adamantane-1-carbonyl)-3-O-(D-2-propionyl-L-alanyl-D-isoglutamine benzyl ester)-α-D-glucopyranoside Step B: 2-Acetamido-2-deoxy-6-O-(adamantane-1-carbonyl)-3-O-(D-2-propionyl-L-alanyl-D-isoglutamine)-D-glucose

EXAMPLE 4

Preparation of
2-Acetamido-6-O-behenoyloxyacetyl-2-deoxy-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of behenoyloxyacetic acid, there are prepared in sequence, Step A: Benzyl-2-acetamido-6-O-behenoyloxyacetyl-2-deoxy-3-O-(D-2-propionyl-L-alanyl-D-isoglutamine benzyl ester)-α-D-glucopyranosid Step B: 2-Acetamido-6-O-behenoyloxyacetyl-2-deoxy-3-O-(D-2-propionyl-L-alanyl-L-alanyl-D-isoglutamine)-D-glucose

EXAMPLE 5

Preparation of
2-Acetamido-6-O-[d-2-(3-chloro-4-cyclohexylphenyl)-propionyl]-2-deoxy-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of d-2-(3-chloro-4-cyclohexylphenyl)propionic acid, there are prepared in sequence, Step A: Benzyl-2-acetamido-2-deoxy-6-O-[d-2-(3-chloro-4-cyclohexylphenyl)propionyl]-2-deoxy-3-O-(D-2-propionyl-L-alanyl-D-isoglutamine benzyl ester)-α-D-glucopyranoside Step B: 2-Acetamido-2-deoxy-6-O-[d-2-(3-chloro-4-cyclohexylphenyl)propionyl-2-deoxy-3-O-(D-2-propionyl-L-alanyl-D-isoglutamine)-D-glucose

EXAMPLE-6

Preparation of 2-Acetamido-2-deoxy-6-O-(N-palmitoyl-L-prolyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of N palmitoyl-L-proline, there are prepared in sequence, Step A: Benzyl-2-acetamido-2-deoxy-6-O-(N-palmitoylprolyl)-3-O-(D-2-propionyl-L-alanyl-D-isoglutamine benzyl ester)-α-D-glucopyranoside Step B: 2-Acetamido-2-deoxy-6-O-(N palmitoyl-L-prolyl-3-O-(D-2-propionyl-D-alanyl-D-isoglutamine)-D-glucose

EXAMPLE 7

Preparation of
2-Acetamido-2-deoxy-6-O-(2-methyl-2-N-palmitoylamidopropionyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of 2-methyl-2-N-palmitoylamido propionic acid, there are prepared in sequence, Step A: Benzyl-2-acetamido-2-deoxy-6-O-(2-methyl-2-N-palmitoylamidopropionyl)-3-O-(D-2-propionyl-L-alanyl-D-isoglutamine benzyl ester)-a-D-glucopyranoside Step B: 2-Acetamido-2-deoxy-6-O-(2-methyl-2-N-palmitoylamidopropionyl)-3-O-(D-2-propionyl-L-alanyl-D-isoglutamine)-D-glucose

EXAMPLE 8

Preparation of
2-acetamido-2-deoxy-6-O-(N-palmitoylglycyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of N-palmitoylglycine, there are prepared in sequence, Step A: Benzyl-2-acetamido-2-deoxy-6-O-(N-palmitoylglycyl)-3-O-(D-2-propionyl-L-alanyl-D-isoglutamine benzyl ester)-α-D-glucopyranoside Step B: 2-Acetamido-2-deoxy-6-O-(N-palmitoylglycyl-3-O-(D-2-propionyl-L-alanyl-D-isoglutamine)-D-glucose

EXAMPLE 9

Preparation of
2-acetamido-2-deoxy-6-O-(N-palmitoylvalyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of N-palmitoyl-L-valine, there are prepared in sequence, Step A: Benzyl-2-acetamido-2-deoxy-6-O-(N-palmitoyl-L-valyl)-3-O-(D-2-propionyl-D-alanyl-D-isoglutamine benzyl ester)-α-D-glucopyranoside Step B: 2-Acetamido-2-deoxy-6-O-(N-palmitoyl-D-valyl)-3-O-(D-2-propionyl-L-alanyl-D-isoglutamine)-D-glucose

EXAMPLE 10

Preparation of 2-acetamido-2-deoxy-6-O-(N palmitoyl-L-phenylalanyl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of N-palmitoyl-L-phenylalanine, there are prepared in sequence, Step A: Eenzyl-2-acetamido-2-deoxy-6-O-(N-palmitoyl-L-phenylalanyl)-3-O-(D-2-propionyl-L-alanyl-D-isoglutamine benzyl ester)-α-D-glucopyranoside Step B: 2-Acetamido-2-deoxy-6-O-(N-palmitoyl-L-phenylalanyl)-3-O-(D-2-propionyl-L-alanyl-D-isoglutamine)-D-glucose

EXAMPLE 11

Preparation of 2-acetamido-2-deoxy-6-O-(N,O-dihexadecyl-D,L-seryl)-3-O-(D-2-propionyl-L-alanyl-D-isoglutamine)-D-glucose Employing the procedure substantially as described in Example 1, but substituting for the behenoyloxyisobutyric acid used in Step A thereof, an equivalent amount of N,O-dihexadecyl-D,L-serine, there are prepared in sequence, Step A: Benzyl-2-acetamido-2-deoxy-6-O-(N,O-dihexadecyl-D,L-seryl)-3-O-(D-2-propionyl-L-alanyl-D-isoglutamine benzyl ester)-a-D-glucopyranoside Step B: 2-Acetamido-L-deoxy-6-O-(N,O-dihexadecy-D,L-seryl)-3-O-(D-2-propionyl-L-alanyl-D-isoglutamine)-D-glucose

EXAMPLE 12

Preparation of 2-acetamido-2-deoxy-6-O-(D,L-2-palmitamido-palmitoyl)-3-O-(D-2-propionyl-L-alanyl-D-isoglutamine)D-glucose Employing the procedure substantially as described in Example 1, but substituting for the behenoyloxyisobutyric acid used in Step A thereof, an equivalent amount of D,L-2-palmitamidopalmitic acid, there are prepared in sequence, Step A: Benzyl-2-acetamido-2-deoxy-6-O-(D,L-2-palmitamidopalmitoyl)-3-O-(D-2-propionyl-L-alanyl-D-isoglutamine benzyl ester)-a-D-glucopyranoside Step B: 2-Acetamido-2-deoxy-6-O-(D,L-2-palmitamidopalmitoyl-3-O-(D-2-propionyl-L-alanyl-D-isoglutamine)-D-glucose

EXAMPLE 13

Preparation of 2-acetamido-2-deoxy-6-O-(N,N'-dipalmitoyl-D-lysyl)-3-O-(D-2-propionyl-L-alanyl-D-isoglutamine)-D-glucose Employing the procedure substantially as described in Example 1, but substituting for the behenoyloxyisobutyric acid used in Step A thereof an equivalent amount of N,N'-dipalmitoyl-L-lysine, there ar prepared in sequence, Step A: Benzyl-2-acetamido-2-deoxy-6-O-(N,N'-dipalmitoyl-L-lysyl-3-O-(D-2-propionyl-L-alanyl-D-isoglutamine benzyl ester)-a-D-glucopyranoside Step B: 2-Acetamido-2-deoxy-6-O-(N,N'-dipalmitoyl-L-lysyl)-3-O-(D-2-propionyl-L-alanyl-D-isoglutamine)-D-glucose

EXAMPLE 14

Preparation of 2-acetamido-2-deoxy-6-O-(N-hexadecanesulfonylglycyl)-3-O-(D-2-propionyl-L-alanyl-D-isoglutamine)-D-glucose Employing the procedure substantially as described in Example 1, but substituting for the behenoyloxyisobutyric acid used in Step A thereof an equivalent amount of N hexadecanesulfonylglycine, there are prepared in sequence, Step A: Benzyl-2-acetamido-2-deoxy-6-O-(N-hexadecanesulfonylglycyl)-3-O-(D-2-propionyl-L-alanyl-D-isoglutamine benzyl ester)-α-D-glucopyranoside Step B: 2-Acetamido-2-deoxy-6-O-(N-hexadecanesulfonylglycyl)-3-O-(D-2-propionyl-L-alanyl-D-isoglutamine)-D-glucose

EXAMPLE 15

Preparation of bis (6-O-muramyl dipeptide) O-palmitoyltartronate

Employing the procedure substantially as described in Example 1, but substituting for the behenoyloxyisobutyric acid used in Step A thereof, half an equivalent amount of O-palmitoyltartronic acid, there are prepared in sequence, Step A: Bis(6-O-muramyl dipeptide α-benzylglucoside benzyl ester) O-palmitoyltartronate Step B: Bis(6-O-muramyl dipeptide) O-palmitoyl tartronate

EXAMPLE 16

Preparation of 2-acetamido-6-O-cholesteryloxycarbonyl-2-deoxy-3-O-(D-2-propionyl-D-alanyl-D-isoglutmine)-D-glucose Step A: Preparation of 2-acetamido-6-O-cholesteryloxycarbonyl-2-deoxy-3-O-(D-2-propionyl-L-alanyl-D-isoglutamine benzyl ester)-a-D-glucopyranoside To benzyl-2-acetamido-2-deoxy-3-O-(D-2-propionyl-L-alanyl-L-isoglutamine benzyl ester)-α-L-glucopyranoside (0.149 mmol) was added dimethylformamide (1 ml.), then dry pyridine (0.62 mmol), then cholesteryl chloroformate (0.16 mmol) and dry dichloromethane (1 ml.). The mixture was stirred at room temperature. After 2 hours, more cholesteryl chloroformate (0.08 mmol) was added and after another hour again more cholesteryl chloroformate (0.16 mmol) was added. After two days at room temperature the mixture was added to dichloromethane (25 ml) and dilute hydrochloric acid (50 ml). The organic layer was separated, dried with magnesium sulfate, and the product purified by preparative thin layer chromatography on silica gel using chloroform/methanol/water: 90/10/1.

Step B: Preparation of 2-acetamido-6-O-cholesteryloxycarbonyl-2-deoxy-3-O-(D-2-propionyl-L-alanyl-D-isoglutamine)-D-glucose To benzyl-2-acetamido-6-O-cholesteryloxycarbonyl-2-deoxy-3-O-(D-2-propionyl-L-alanyl-D-isoglutamine benzyl ester)-α-D glucopyranoside (0.096 mmol) was added acetic acid (5 ml.), and palladium oxide (100 mg.) and this mixture was shaken in a hydrogen atmosphere for two days. The catalyst was removed by filtration and the solvent evaporated to give the product.

EXAMPLE 17

Preparation of methyl-2-acetamido-2-deoxy-6-O-hexadecyloxycarbonyl-3-O-(D-2-propionyl-L-alanyl-D-isoglutamine)-β-D-glucopyranoside Step A: Preparation of methyl-2-acetamido-2-deoxy-6-O-hexadecyloxycarbonyl-3-O-(D-2-propionyl L-alanyl-D-isoglutamine benzyl ester)-β-D-glucopyranoside To dry dichloromethane (3 ml.) was added phosgene in benzene (0.55 mmol), 1-hexadecanol (0.50 mmol) and pyridine (0.1 ml). This mixture was then added to a stirred solution of methyl-2-acetamido-2-deoxy-3-O-(D-2-propionyl-L-alanyl-D-isoglutamine benzyl ester)-β-D-glucopyranoside (0.276 mmol) in dimethylformamide (3 ml). After one day at room temperature the mixture was added to dichloromethane (25 ml) and dilute hydrochloric acid (50 ml). The organic phase was separated, dried with magnesium sulfate, and the product purified by preparative thin layer chromatography on silica gel using chloroform/methanol/water: 85/15/1.5.

Step B: Preparation of methyl-2-acetamido-2-deoxy-6-O-hexadecyloxycarbonyl-3-O-(D-2-propionyl-L-alanyl-D-isoglutamine)-β-D-glucopyranoside To methyl-2-acetamido-2-deoxy-6-O-hexadecyloxycarbonyl-3-O-(D-2-propionyl-D-alanyl-isoglutamine benzyl ester)-β-D-glucopyranoside (0.034 mmol) was added acetic acid (5 ml), palladium oxide (100 mg) and this mixture was shaken in a hydrogen atmosphere for 18 hours. The catalyst was removed by filtration and

EXAMPLE 18

Preparation of methyl-2-acetamido-6-O-behenoyloxyisobutyryl-2-deoxy-3-O-(D-2-propionyl-L-alanyl-D-isoglutamine)-β-D-glucopyranoside Employing the procedure substantially as described in Example 1, but substituting for the benzyl2-acetamido-2-deoxy-3-O-(D-2-propionyl-L-alanyl-D-isoglutamine benzyl ester)-α-D-glucopyranoside used in Step A thereof, an equivalent amount of methyl-2-acetamido-2-deoxy-3-O-(D-2-propionyl-L-alanyl-D-isoglutamine benzyl ester)-β-D-glucopyranoside, there are prepared in sequence, Step A: Methyl 2-acetamido-6-O-behenoyloxyisobutyryl-2-deoxy-3-O-(D-2-propionyl-L-alanyl-D-isoglutamine benzyl ester)-β-D-glucopyranoside Step B: Methyl 2-acetamido-6-O-behenoyloxyisobutyryl-2-deoxy-3-O-(D-2-propionyl-L-alanyl-D-isoglutamine)-β-D-glucopyranoside

EXAMPLE 19

Preparation of 2-acetamido-2-deoxy-6-O-(16-hydroxyhexadecanoyl)-3-O-(D-2-propionyl-L-alanyl-D-isoglutamine)-D-glucose Step A: Preparation of benzyl-2-acetamido-2-deoxy-6-O-(16-hydroxyhexadecanoyl)-3-O-(D-2-propionyl-L-alanyl-D-isoglutamine benzyl ester)-a-D-glucopyranoside To a stirred solution of 16 hydroxyhexadecanoic acid (135 mg., 0.50 mmol)in dry N,N-dimethylformamide (4 ml. were added 4 dimethylaminopyridine (6 mg.) and benzyl-2-acetamido-2-deoxy-3-O-(D-2-propionyl-L-alanyl-D-isoglutamine benzyl ester)-glucopyranoside (300 mg., 0.45 mmol). The reaction mixture was cooled in an ice bath, and N,N'-dicyclohexylcarbodiimide (DCC) (102 mg., 0.49 mmol) was added. After stirring for 5 hours at room temperature, additional 16-hydroxyhexadecanoic acid (135 mg. and DCC (102 mg. were added. The reaction mixture was then stirred overnight at room temperature. The precipitated solid was filtered, the filtrate evaporated, the residue taken up in chloroform, washed twice with 0.5 M hydrochloric acid and once with saturated aqueous sodium hydrogen-carbonate. The organic layer was evaporated, the residue dissolved in the minimal volume of chloroform, the solution applied to a column of silica gel (Merck No. 7734) that was eluted with 20:1 chloroform-methanol. Evaporation of the appropriate fractions gave benzyl-2-acetamido-2-deoxy-6-O-(16-hydroxyhexadecanoyl)-3-O-(D-2-propionyl-L-alanyl-D-isoglutamine benzyl ester)-αD-glucoypyranoside as a chromatographically homogeneous solid, yield 103 mg. (25%).

The 300 MHz NMR spectrum in dimethyl sulfoxide-$d_6$ was in accord with the desired structure.

Step B: Preparation of 2-acetamido-2-deoxy-6-O-(16-hydroxhexadecanoyl)-3-O-(D-2-propionyl-L-alanyl-D-isoglutamine)-D-glucose A solution of benzyl-2-acetamido-2-deoxy-6-O-(16-hydroxyhexadecanoyl)-3-O-(D-2-propionyl-L-alanyl-D-isoglutamine benzyl ester)-αD-glucopyranoside (93 mg.) in glacial acetic acid (3 ml.) was hydrogenolyzed for 48 hours at atmospheric pressure and room temperature in the presence of palladium (added as PdO, 150 mg.). The reaction mixture was filtered through Celite, the filtrate evaporated and coevaporated several times with toluene. The residue was dissolved in the minimal volume of chloroform methanol (9:1) and the solution was applied to a column of silica gel (Merck No. 7734) that was eluted with initially 9:1 chloroform methanol, then 80:20:2 chloroform-methanol water. The fractions containing the desired product were combined and evaporated and the resulting solid coevaporated several times with diethyl ether and dried in vacuo over phosphorus pentoxide to afford pure 2-acetamido-2-deoxy-6-O-(16-hydroxyhexadecanoyl)-3-O-(D-2-propionyl-L-alanyl-D-isoglutamine)-D-glucose; yield-64 mg. (85%).

The 300 MHz NMR spectrum in dimethyl sulfoxide-$d_6$ was in accord with the desired structure.

EXAMPLE 20

Preparation of 2-acetamldo-6-O-(16-acetoxyhexadecanoyl)-4-O-acetyl-3-O-(D-2-propionyl-L-alanyl-D-isoglutamine-D-glucose Step A: Preparation of benzyl-2-acetamido-6-O-(16-acetoxyhexadecanoyl)-4-O-acetyl-3-O-(D-2-propionyl-L-alanyl-D-isoglutamine)-benzyl ester)-a-D-glucopyranoside To a solution of benzyl-2-acetamido-2-deoxy-6-O-(16-hydroxyhexadecanoyl)-3-O-(D-2-propionyl-L-alanyl-D-isoglutamine benzyl ester)-α-D-glucopyranoside (103 mg.) in pyridine (1 ml.) was added acetic anhydride (0.5 ml.). The reaction mixture was stirred overnight at room temperature, evaporated, and coevaporated several times with toluene. The resulting solid was dried in vacuo to afford benzyl-2-acetamido-6-O-(16-acetoxyhexadecanoyl)-4-O-acetyl-2-deoxy-3-O-(D-2-propionyl-L-alanyl-D-isoglutamine benzyl ester)-α-D-glucopyranoside, yield 112 mg. (quantitative).

The 300-MHz NMR spectrum in dimethylsulfoxide-$d_6$ was in accord with the desired structure.

Step B: Preparation of 2-acetamido-6-O-(16-acetoxyhexadecanoyl)-4-O-acetyl-2-deoxy-3-O-(D-2-propionyl-L-alanyl-D-isoglutamine)-D-glucose A solution of benzyl-2-acetamido-6-O-(16-acetoxyhexadecanoyl)-4-O-acetyl-2-deoxy-3-O-(D-2-propionyl-L-alanyl-D-isoglutamine benzyl ester)-α-D-glucopyranoside (110 mg.) in glacial acetic acid (5 ml.) was hydrogenolyzed for 24 hours at atmospheric pressure and room temperature in the presence of palladium (added as PdO, 150 mg The reaction mixture was filtered through Celite, the filtrate evaporated, coevaporated several times with water and toluene. The resulting solid was dried in vacuo over phosphorus pentoxide to afford 2-acetamido-6-O-(16-acetoxyhexadecanoyl)-4-O-acetyl-2-deoxy-3-O-(D-2-propionyl-L-alanyl-D-isoglutamine)-D-glucose: yield 50 mg. (56%). The 300-NHz NMR spectrum in dimethylsulfoxide-$d_6$ was in accord with the desired structure.

EXAMPLE 21

Preparation of 2-acetamido-2-deoxy-6-O-(2-furoyl)-3-O-(D-2-propionyl-L-alanyl-D-isoglutamine)-D-glucose Step A: Preparation of benzyl-2-acetamido-2-deoxy-6-O-(2-furoyl)-3-O-(D-2-propionyl-L-alanyl-D-isoglutamine benzylester)-α-D-glucopyranoside To a stirred solution of 2 furoic acid (42 mg., 0 37 mmol) in dry N,N-dimethylformamide (2 ml.) were added 4-dimethylaminopyridine (5 mg. and benzyl 2-acetamido-2-deoxy-3-O-(D-2-propionyl-L-alanyl-D-isoglutamine benzylester)-α-D-glucopyranoside (250 mg., 0.37 mmol). The reaction mixture was cooled in an ice bath and N,N dicyclohexylcarbodiimide (DCC) (77 mg., 0.37 mmol) added. After stirring for 4 hours at room temperature, additional 2-furoic acid (42 mg.) and DCC (77 mg. were added. The reaction mixture was stirred overnight at room temperature. The precipitated solid gas filtered and the filtrate evaporated. The residue was taken up in dichloromethane, washed twice with 0.5 M hydrochloric acid and once with saturated aqueous sodium hydrogen carbonate. The organic layer was evaporated to a syrup that was dissolved in the minimal volume of chloroform and the solution applied to a column of silica gel (Merck No. 7734) that was eluted with 17:1 chloroform methanol. Evaporation of the appropriate fractions gave benzyl-2-acetamido-2-deoxy-6-O-(2-furoyl-3-O-(D-2-propionyl-L-alanyl-D-isoglutamine benzyl ester)-α-D-glucopyranoside as a syrup that solidified upon trituration with diethyl ether; yield 95 mg. (33%).

The 300 MHz NMR spectrum in dimethylsulfoxide-$d_6$ was in accord with the desired structure.

Step B: 2-acetamido-2-deoxy-6-O-(2-furoyl)-3-O-(-D-2-propionyl-L-alanyl-D-isoglutamine)-D-glucose A solution of benzyl-2-acetamido-2-deoxy-6-O-(2-furoyl)-3-O-(D-2-propionyl-L-alanyl-D-isoglutamine benzyl ester)-α-D-glucopyranoside (93 mg.) in glacial acetic acid (5 ml.) was hydrogenolyzed at atmospheric pressure and room temperature in the presence of palladium (added as PdO, 150 mg.). The reaction mixture was filtered through Celite, the filtrate evaporated, and coevaporated several times with water and toluene. The residue was dissolved in the minimal volume of methanol, filtered, and the product precipitated by addition of diethyl ether. The solid was filtered and dried in vacuo over phosphorus pentoxide; yield 60 mg. (85%).

The 300-MHz NMR spectrum in deuterium oxide was in accord with the desired structure.

EXAMPLE 22

Preparation of
2-acetamido-2-deoxy-4,6-di-O-methoxy-acetyl-3-O-(D-2-propionyl-L-alanyl-D-isoglutamine)-D-glucose Step A: Preparation of benzyl-2-acetamido-2-deoxy-4,6-di-O-methoxyacetyl-3-O-(D-2-propionyl-L-alanyl-D-isoglutamine benzyl ester)-a-D-glucopyranoside To a solution of methoxyacetic acid (69 μl., 0.90 mmol) in dry N,N-dimethylformamide (3 ml.) were added 4-dimethylaminopyridine (11 mg.) and benzyl-2-acetamido-2-deoxy-3-O-(D-2-propionyl-L-alanyl-D-isoglutamine benzyl ester)-α-D-glucopyranoside (300 mg., 0.45 mmol). After cooling in an ice bath, N,N'-dicyclohexylcarbodiimide (DCC) (190 mg., 0.92 mmol) was added. After stirring for 4 hours at room temperature, additional methoxyacetic acid (69 μl) and DCC (190 mg.) were added. The reaction mixture was stirred overnight at room temperature, concentrated, the residue taken up in dichloromethane, washed twice with 0.5 M hydrochloric acid, once with saturated sodium hydrogencarbonate, and evaporated. The residue was dissolved in the minimal volume of chloroform and the solution applied to a column of silica gel (Merck No. 7734) that was eluted with 23:1 chloroform methanol. The fractions containing the desired product were combined and evaporated to give benzyl-2-acetamido-2-deoxy-4,6-di-O-methoxyacetyl-3-O-(D-2-propionyl-L-alanyl-D-isoglutamine benzyl ester)-α-D-glucopyranoside; yield 317 mg. (87%).

The 300-MHz NMR spectrum in dimethylsulfoxide-$d_6$ was in accord with the desired structure.

Step B: Preparation of 2-acetamido-2-deoxy-4,6-di-O-methoxyacetyl-3-O-(D-2-propionyl-L-alanyl-D-isoglutamine)-L-glucose A solution of benzyl-2-acetamido-2-deoxy-4,6-di-O-methoxyacetyl-3-O-(D-2-propionyl-L-alanyl-D-isoglutamine benzyl ester)-α-D-glucopyranoside (225 mg.) in glacial acetic acid (8 ml.) was hydrogenolyzed for 96 hours at atmospheric pressure and room temperature in the presence of palladium (two 100 mg. additions as PdO). The catalyst was removed by filtration throuqh Celite, the filtrate was evaporated and coevaporated several times with toluene. The residue was purified by chromatography on a column of silica gel (Merck No. 7734) and elution with 80:20:2 and subsequently with 70:30:3 chloroform-methanol water. The resulting syrup was dissolved in the minimal volume of methanol and the product was precipitated by addition of diethyl ether. The solid was filtered and dried in vacuo over phosphorus pentoxide; yield 82 mg. (47%).

The 300-MHz NMR spectrum in deuterium oxide was in accord with the desired structure.

EXAMPLE 23

Preparation of
2-acetamido-4,6-di-O-acetamidoacetyl-2-deoxy-3-O-(D-2-propionyl-L-alanyl-D-isoglutamine)-D-glucose Step A: Preparation of benzyl-2-acetamido-4,6-di-O-acetamidoacetyl-2-deoxy-3-O-(D-2-propionyl-L-alanyl-D-isoglutamine benzyl ester)-a-D-glucopyranoside In like manner as Step A in Example 23, substituting a stoichiometric equivalent amount of acetamidoacetic acid for methoxyacetic acid, there was obtained benzyl-2-acetamido-4,6-di-O-acetamidoacetyl-2-deoxy-3-O-(D-2-propionyl-L-alanyl-D-isoglutamine benzyl ester)-α-D-glucopyranoside.

Step B: Preparation of 2-acetamido-4,6-di-O-acetamidoacetyl-2-deoxy-3-O-(D-2-propionyl-L-alanyl-D-isoglutamine)-D-glucose A solution of benzyl-2-acetamido-4,6-di-O-acetamidoacetyl-2-deoxy-3-O-(D-2-propionyl-L-alanyl-D-isoglutamine benzyl ester)-α-D-glucopyranoside (71 mg.) in glacial acetic acid (5 ml.) was hydrogenolyzed for 24 hours at atmospheric pressure and room temperature in the presence of palladium (added as PdO, 100 mg.). The catalyst was removed by filtration through Celite, the filtrate evaporated and coevaporated several times with toluene. The residue was dissolved in the minimal volume of methanol and the product precipitated by addition of diethyl ether. The filtered solid was dissolved in a small volume of water and lyophilyzed to afford 2-acetamido-4,6 di-O-acetamidoacetyl-2deoxy-3-O-(D-2-propionyl-L-alanyl-D-isoglutamine)-D-glucose as an amorphous solid, yield 43 mg.(77%).

The 300-MHz NMR spectrum in deuterium oxide was in accord with the desired structure.

EXAMPLE 24

Preparation of
2-acetamido-2-deoxy-6-O-(5-ketohexanoyl)-3-O-(D-2-propionyl-L-alanyl-D-isoglutamine)-D-glucose Step A: Preparation of benzyl-2-acetamido-2-deoxy-6-O-(5-ketohexanoyl)-2-O-(D-2-propionyl-L-alanyl-D-isoglutamine benzyl ester)-a-D-glucopyranoside To a solution of 5-ketohexanoic acid (61 mg., 0.47 mmol) in dry N,N-dimethylformamide (3 ml.) were added 4-dimethylaminopyridine (5.5 mg.) and benzyl 2-acetamido-2-deoxy-3-O-(D-2-propionyl-L-alanyl-D-isoglutamine benzyl ester)-α-D-glucopyranoside (300 mg., 0.45 mmol). After cooling in an ice bath, N,N'-dicyclohexylcarbodiimide (DCC) (98 mg., 0.47 mmol) was added. After stirring for 5 hours at room temperature, a second addition of 5-ketohexanoic acid (61 mg.) and DCC (98 mg.) was made. The reaction mixture was stirred overnight at room temperature, the precipitated solid filtered, and the filtrate evaporated. The product was isolated by chromatography on a column of silica gel and elution with 24:1 dichloromethane methanol. Benzyl-2-acetamido-2-deoxy-6-O-(5-ketohexanoyl)-3-O-2-propionyl-L-alanyl-D-isoglutamine benzyl ester glucopyranoside was obtained as a white amorphous solid; yield 213 mg. (61%).

The 300-MHz NMR spectrum in dimethylsulfoxide-$d_6$ was in accord with the desired structure.

Step B: Preparation of 2-acetamido-2-deoxy-6-O-(5-ketohexanoyl)-3-O-(D-2-propionyl-L-alanyl-D-isoglutamine)-D-glucose A solution of benzyl-2-acetamido-2-deoxy-6-O-(5-ketohexanoyl)-3-O-(D-2-propionyl-L-alanyl-D-isoglutamine benzyl ester)-α-D-glucopyranoside (210 mg.) in glacial acetic acid (5 ml.) was hydrogenolyzed for 48 hours at atmospheric pressure and room temperature in the presence of palladium (added as PdO, 100 mg.. The catalyst was removed by filtration through Celite, the filtrate evaporated and coevaporated several times with toluene. The residue was taken up in a small volume of ethanol and the product precipitated by addition of diethyl ether. The solid was filtered, dissolved in a small volume of water, and lyophilyzed. 2-Acetamido-2-deoxy-6-O-(5-ketohexanoyl)-3-O-(D-2-propionyl-L-alanyl-D-isoglutamine)-D-glucose was obtained as a white solid; yield 130 mg. (80%).

The 300-MHz NMR spectrum in deuterium oxide was in accord with the desired structure.

It is reasonably believed on the basis of the data that the disclosed invention pharmaceutical compounds herein alone, or in combination with an anti AIDS drug, will provide a human host who is immunocompromised as a result of infection or contact with an AIDS related virus, with enhanced host resistance to opportunistic bacterial, fungal or viral infection, including the conditions of Kaposi's sarcoma and Pneumocystis pneumonia.

What is claimed is:

1. A composition for enhancing host resistance against opportunistic bacterial, fungal or viral infection in a human host immunocompromised by an AIDS-related virus comprising a compound of the formula:

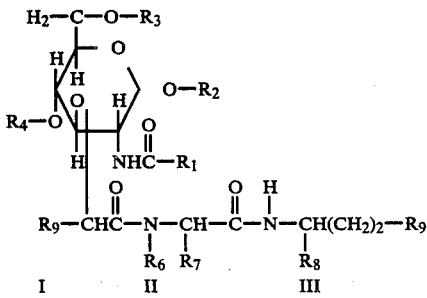

wherein:

$R_1$ is $C_{1-7}$ alkyl; $C_{1-7}$ alkyl substituted by hydroxy, mercapto, alkoxy of 1–3 carbons, alkyl mercapto of 1–3 carbons, hydroxy or mercapto esterified by an acid of 1–4 carbon atoms, halogen, carboxyl, or carboxyl functionally modified by esterification with a lower alcohol of 1–3 carbons or by amidation; phenyl; or phenyl substituted by one or more alkyl groups of 1–3 carbon atoms or hydroxy or mercapto groups either free or etherified by an acid of 1–4 carbons, alkylidioxy of 1–4 carbons, cycloalkyldioxy of 5–7 carbon atoms, amino, or trifluoromethyl;

$R_2$ is hydrogen; $C_{1-7}$ alkyl; $C_{1-7}$ alkyl substituted by hydroxy, mercapto, alkoxy of 1–3 carbons, alkyl mercapto of 1–3 carbons, hydroxy mercapto esterified by an acid of 1–4 carbon atoms, halogen, carboxyl, or carboxyl functionally modified by esterification with a lower alcohol of 1–3 carbons or by amidation; phenyl; phenyl substituted by one or more alkyl groups of 1–3 carbon atoms or hydroxy or mercapto groups either free or etherified by an alkyl group of 1–3 carbons or esterified by an acid of 1–4 carbons, alkyldioxy of 1–4 carbons, cycloalkyldioxy of 5–7 carbon atoms, amino, or triifluoromethyl; phenyl $C_{1-4}$ alkyl; or phenyl $C_{1-4}$ alkyl substituted by one or more alkyl groups of 1–3 carbon atoms or hydroxy or mercapto groups either free or etherified by an alklyl group of 1–3 carbons or esterified by an acid of 1–4 carbons, alkyldioxy of 1–4 carbons, cycloalkyldioxy of 5–7 carbon atoms, amino, or trifluoromethyl;

$R_3$ and $R_4$ may be the same or different and are each independently hydrogen, provided that $R_3$ and $R_4$ may not both be hydrogen; or

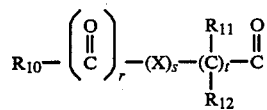

where
X is —O—; —S—; or

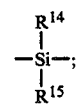

$R_{10}$ is hydrogen; $C_{1-30}$ alkyl; $C_{2-30}$ alkenyl; $C_{1-30}$ alkoxy; phenyl; $C_{1-20}$ alkylsulfonyl; or cholesteryl;

$R_{11}$, $R_{12}$, $R_{14}$, and $R_{15}$ may be the same or different and are each independently hydrogen; $C_{1-20}$ alkyl; $C_{1-20}$ alkylcarbonyloxy; amino; benzyl; $C_{1-20}$ alkoxy-methyl; $C_{1-20}$ alkylamido; or

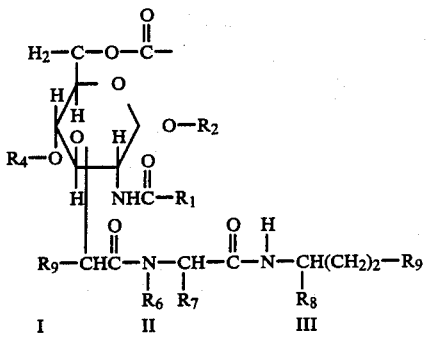

r is 0 or 1; s is 0 or 1; and t is 0 to 20; provided that s may only be 0 when both r and t are greater than 0 or when r is 0 and $R_{10}$ is amino; phenyl; substituted phenyl; 1-adamantyl or hetero-cycle selected from the group consisting of 2- or 3-furyl, 2- or 3- thienyl, 2- or 3- pyrrolidinyl, 2-, 3- or 4- pyridyl, and 1-tetrazolyl, said heterocycle optionally substituted with $C_{1-20}$ alkylcarbonyl; and where $R_3$ or $R_4$ is other than hydrogen, the other of $R_3$ or $R_4$ may additionally be $C_{1-4}$ alkylcarbonyl;

$R_5$ is hydrogen or $C_{1-10}$ alkyl;

$R_6$ is hydrogen or $R_6$ and $R_7$ taken together are $-(CH_2)_3$;

$R_7$ is hydrogen; $C_{1-7}$ allkyl; hydroxymethyl; mercaptomethyl; benzyl; or substituted benzyl;

$R_8$ and $R_9$ may be the same or different and are each independently COOR, or CONR'R", where R is hydrogen or $C_{1-7}$ alkyl, and R' and R" are hydrogen or $C_{1-3}$ alkyl;

when $R_5$ is $C_{1-10}$ alkyl, the stereochemistry at asymmetric center I is D or L;

when $R_7$ is other than hydrogen, the stereochemistry at asymmetric center II is L; and the stereochemistry at asymmetric center III is D; and acid addition and quaternary salts thereof; or pharmaceutically acceptable acid addition salts thereof; and an antiviral, anti-aids drug selected from the group consisting of azidothumidine, ansamycin, ribavirin, deoxycytidine, HPA-23,-AL-721, foscarnet, in a physiologically acceptable medium in an amount effective to impart resistance against bacterial, fungal or viral infection.

2. The composition of claim 1 wherein said compound is selected from:

2-acetamido-6-O-behenoyloxyisobutyryl-2-deoxy-3-O-(D-2-propionyl-L-alanyl-D-isoglutamine)-D-glucose;
2-acetamido-2-deoxy-6-O-(N,O-dipalmitoyl-D,L-seryl)-3-O-(D-2-propionyl-L-alanyl-D-isoglutamine)-D-glucose;
2-acetamido-6-O-(adamantane-1-carbonyl)-3-O-(D-2-propionyl-L-alanyl-D-isoglutamine)-D-glucose;
2-acetamido-6-O-behenoyloxyacetyl-2-deoxy-3-O-(D-2-propionyl L-alanyl-D-isoglutamine)-D-glucose;
2-acetamido-6-O-[d-2-(3-chloro-4-cyclohexylphenyl)propionyl]-2-deoxy-3-O-(D-2-propionyl-L-alanyl-D-isoglutamine)-D-glucose;
2-acetamido-2-deoxy-6-O-(N-palmitoyl-L-prolyl)-3O-(D-2-propionyl-L-alanyl-D-isoglutamine)-D-glucose;
2-acetamido-2-deoxy-6-O-(2-methyl-2-N-palmitoylamidopropionyl-3-O-(D-2-propionyl-L-alanyl-D-isoglutamine)-L-glucose;
2-acetamido-2-deoxy-6-O-(N-palmitoylglycyl)-3-O-(D-2-propionyl-L-alanyl-D-isoglutamine)-D-glucose;
2-acetamido-2-deoxy-6-O-(N-palmitoyl-L-valyl)-3-O-(D-2-propionyl-L-alanyl-D-isoglutamine)-D-glucose;
2-acetamido-2-deoxy-6-O-(N-palmitoyl-D-phenylalanyl)-3-O-(D-2-propionyl-L-alanyl-D-isoglutamine)-D-glucose;
2-acetamido-2-deoxy-6-O-(N,O-dihexadecyl-D,L-seryl)-3-O-(D-2-propionyl-L-alanyl-D-isoglutamine)-D-glucose;
2-acetamido-2-deoxy-6-O-(D,L-2-palmitamidopalmitoyl)-3-O-(D-2-propionyl-L-alanyl-D-isoglutamine)-D-glucose;
2-acetamido-2-deoxy-6-O-(N,N'-dipalmitoyl-D-lysyl)-3-O-(D-2-propionyl-L-alanyl-D-isoglutamine)-D-glucose;
2-acetamido-2-deoxy-6-O-(N-hexadecanesulfonylglycyl)-3-O-(D-2-propionyl-L-alanyl-D-isoglutamine)-D-glucose;
Bis(6-O-muramyl dipeptide)O-palmitoyltartronate;
2-acetamido-6-O-cholesteryloxycarbonyl-2-deoxy-3-O-(D-2-propionyl-L-alanyl-D-isoglutamine)-D-glucose;
Methyl 2-acetamido-2-deoxy-6-O-hexadecyloxycarbonyl-3-O-(D-2-propionyl-L-alanyl-D-isoglutamine)-β-D-glucopyranoside;
Methyl 2-acetamido-6-O-behenoyloxyisobutyryl-2-deoxy-3-O-(D-2-propionyl-L-alanyl-D-isoglutamine)-β-D-glucopyranoside;
2-acetamido-2-deoxy-6-O-(16-hydroxyhexadecanoyl)-3-O-2-propionyl-L-alanyl-D-isoglutamine)-D-glucose;
2-acetamido-6-O-(16-acetoxyhexadecanoyl)-4-O-acetyl-3-O-(D-2-propionyl-L-alanyl-D-isoglutamine)-D-glucose;
2-acetamido-2-deoxy-6-O-(2-furoyl)-3-O-(D-2-propionyl-L-alanyl-D-isoglutamine)-D-glucose;
2-acetamido-2-deoxy-4,6-di-O-methoxyacetyl-3-O-(D-2-propionyl-L-alanyl-D-isoglutamine)-D-glucose;
2-acetamido-4,6-di-O-acetamidoacetyl-2-deoxy-3-O-2-propionyl-L-alanyl-D-isoglutamine)-D-glucose;
2-acetamido-2-deoxy-6-O-(5-ketohexanoyl)-3-O-(D-2-propionyl-L-alanyl-D-isoglutamine)-D-glucose;
2-acetamido-6-O-(6-aminohexanoyl)-2-deoxy-3-O-(D-2-propionyl-L-alanyl-D-isoglutamine)-D-glucose;
2-acetamido-6-O-(6-acetamidohexanoyl)-2-deoxy-3-O-(D-2-propionyl-L-alanyl-D-isoglutamine)-D-glucose;
2-acetamido-2-deoxy-6-O-(phenylacetyl)-3-O-(D-2-propionyl-L-alanyl-D-isoglutamine)-D-glucose;
2-acetamido-2-deoxy-6-O-(phenoxyacetyl)-3-O-(D-2-propionyl-L-alanyl-D-isoglutamine)-D-glucose;
2-acetamido-2-deoxy-6-O-(ethoxycarbonyl)-3-O-(D-2-propionyl-L-alanyl-D-isoglutamine)-D-glucose;
2-acetamido-2-deoxy-6-O-(1-tetrazolylacetyl)-3-O-2-propionyl-L-alanyl-D-isoglutamine)-D-glucose.

3. A method for enhancing host resistance against opportunistic bacterial, fungal or viral infection in a human host immunocompromised by an AIDS-related virus comprising a composition containing the step of administering to said host a compound according to claim 1.